United States Patent
De Moyer

(10) Patent No.: US 8,439,675 B2
(45) Date of Patent: May 14, 2013

(54) METHOD FOR PRODUCING A BONE PROSTHESIS OR A PRE-IMPLANT SIMULATION, AND EQUIPMENT USED

(75) Inventor: Philippe Albert Paul Ghislain De Moyer, Beersel (BE)

(73) Assignee: 2 Ingis S.A., Brussels (BE)

( * ) Notice: Subject to any disclaimer, the term of this patent is extended or adjusted under 35 U.S.C. 154(b) by 776 days.

(21) Appl. No.: 12/373,295

(22) PCT Filed: Jul. 9, 2007

(86) PCT No.: PCT/EP2007/056957
§ 371 (c)(1),
(2), (4) Date: Jan. 9, 2009

(87) PCT Pub. No.: WO2008/006802
PCT Pub. Date: Jan. 17, 2008

(65) Prior Publication Data
US 2010/0004698 A1    Jan. 7, 2010

(30) Foreign Application Priority Data

Jul. 11, 2006  (EP) .................................... 06116963

(51) Int. Cl.
*A61C 3/00*  (2006.01)
(52) U.S. Cl.
USPC ................................. 433/75; 433/72; 606/96
(58) Field of Classification Search ............. 606/96; 433/72, 75–76
See application file for complete search history.

(56) References Cited

U.S. PATENT DOCUMENTS

| | | | |
|---|---|---|---|
| 2,621,408 A | 12/1952 | Klein | |
| 5,207,753 A | 5/1993 | Badrinath | |
| 5,954,769 A | 9/1999 | Rosenlicht | |
| 2008/0153060 A1* | 6/2008 | De Moyer | 433/173 |

FOREIGN PATENT DOCUMENTS

| | | |
|---|---|---|
| DE | 29705088 | 5/1997 |
| EP | 0328911 | 8/1989 |
| EP | 0930050 | 7/1999 |
| EP | 1547544 | 6/2005 |
| JP | 63-216560 | 9/1988 |
| JP | 2001-212158 | 8/2001 |
| WO | WO 98/43528 | 10/1998 |
| WO | WO 00/74585 | 12/2000 |
| WO | WO 2004/075771 | 9/2004 |
| WO | WO 2006/082198 | 8/2006 |
| WO | WO 2007/085719 | 8/2007 |

\* cited by examiner

*Primary Examiner* — Andrew Yang
*Assistant Examiner* — Olivia C Chang
(74) *Attorney, Agent, or Firm* — Christopher Casieri

(57) ABSTRACT

Method for producing a bone prosthesis, comprising forming a surgical guide (1) equipped with at least one artificial prosthesis (150 and with at least a first hole passing through each artificial prosthesis in a predetermined orientation, placing the surgical guide on a model (2), drilling a second hole (16) through the model with the aid of a drill (8) passed through each first hole, the passage of the drill through the corresponding first hole taking place without contact therewith, and guiding the drill in said predetermined orientation with the aid of drill introduction means (10, 11) situated outside said first hole.

6 Claims, 4 Drawing Sheets

1

METHOD FOR PRODUCING A BONE PROSTHESIS OR A PRE-IMPLANT SIMULATION, AND EQUIPMENT USED

This application is a 371 application of PCT/EP2007/056957, filed Jul. 9, 2007, which, in turn, claims priority of European Patent Application No. EP 06116963.7, filed on Jul. 11, 2006.

The present invention relates to a method for producing a bone prosthesis to be implanted in a bone of a patient and to equipment used for such an implantation.

The method and the equipment according to the invention are more particularly designed for the application of dental or hearing implants.

Dental implants are for the time being applied in four ways:
1. Free hand with a large cut in the skin or the gingiva and in the periosteum and their separation. The drilling is carried out in an antiquated manner without any spatial marker relating to the future prosthesis. Although this technique is the worst and provides results that are often esthetically, functionally and hygienically disastrous, it is the most used technique. It is also that which causes the most accidents (rupture of the mandibular nerve, arterial rupture, piercing the sinus, breaking cortical bones, etc.).
2. Free hand with a large cut in the gingiva and in the periosteum and a separation of the latter. The drilling is carried out in a more or less precise manner, as the dental laboratory has produced a surgical guide that more or less prefigures the future prosthesis. This technique is the second most used, but the drawback is that the surgical guide does not contain any spatial marking information. In addition, it often cannot be used in view of the cutting of the gingiva which prevents the placement of the latter. With this technique results are often bad in esthetic, functional and hygienic terms, and there are many accidents such as those previously mentioned.
3. With the hand guided by drilling guides produced from computerized plans. This technique makes it possible to place drilling cylinders in these guides at precise locations depending on the bone or depending on the bone and the future prosthesis. Three distinct technologies apply this technique:

Guides are produced from stereolithographic models, that is to say on the basis of images from a dental scan in DICOM form. Artifacts often disturb the production of these guides by not always allowing them to be used through lack of precision.

A guide is produced from an impression and from a radiological guide which is made on the basis of this silicone impression. A scan is carried out of the patient with the guide in the mouth and of the guide alone. A surgical guide is then produced from DICOM images and transformed by inserting guiding cylinders for the drilling and the application of implants into the jaw. Here too, artifacts disturb the production of these guides.

Radiological guides then transformed into surgical guides are produced as described in the previously filed patent application PCT/EP2006/050584.

These techniques allow harm to the patient to be reduced and the latter technique in particular improves the prosthetic result.
4. Free hand guided by a navigation system (GPS). This technique enables an implant to be located more or less with precision. But it does not enable all harm to the patient to be prevented, as the drilling remains manual and a slip remains possible. In addition, it does not take account of the future prosthesis. This technique is expensive and is the least used.

All these techniques, with the exception of that in which a scan is done with the guide in the patient's mouth and a separate scan of the guide and that described in the patent application PCT/EP2006/050584, have the drawback of having to produce the final prosthesis after making an impression of the jaw where the implants have previously been placed, which making of an impression is carried out several weeks after the application of the implants, which is complex and requires numerous post-operative interventions that are burdensome for the patient.

Furthermore, some of the aforementioned techniques foresee drilling, whether in a model or in the patient's jaw, through guiding cylinders that guide the drill during its penetration. This operation has several major disadvantages, among others the possibility of blockage of the part guiding the drill in the cylinder if the insertion axis is poorly chosen, braking of the motor of the drilling apparatus through friction with the inner wall of the guiding cylinder, premature wear of the motor, wear in the guiding cylinder with the risk of scattering metal particles into the operation site, heating of the drill or of the guiding cylinder with the possibility of burns at the bone level.

The aim of the present invention is to develop a method and equipment for producing a bone prosthesis that can be made in a final manner on a model, even before application of the implants, and to place this prosthesis on the implants, the day these are applied in the bone of the patient, especially as described in the aforementioned patent application PCT/EP2006/050584, while simultaneously avoiding the drawbacks mentioned above.

In order to solve this problem, according to the invention, a method is provided for producing a bone prosthesis to be implanted in a patient's bone, comprising:
   production, from an impression of the skin or mucous membranes of the patient, of a surgical guide equipped with at least one artificial prosthesis and at least one first hole, each passing through an aforementioned artificial prosthesis in a predetermined direction;
   placement of the surgical guide on a model obtained from said impression;
   drilling through the model of a second hole using a drill passed through each first hole, the second hole having the predetermined direction of its corresponding first hole;
   placement, in each drilled second hole, of an implant analog having dimensions corresponding to those of a real implant to be placed in the patient's bone, this placement being carried out by means of an analog holder passed through the corresponding first hole;
   fixing the implant analog in its second hole, as placed; and
   after removal of each analog holder and of the surgical guide, construction of a final bone prosthesis matching the model provided with the implant analog(s) and intended to be fixed to one or more real implants after their implantation in the patient's bone using the surgical guide in a similar manner to that used for placing implant analogs in the model.

This method is characterized in that it furthermore comprises:
   during the drilling of a second hole, passage of the drill and/or an extension element extending this drill through the corresponding first hole without contact with it; and
   guiding the drill in said predetermined direction using means for inserting the drill situated outside said first hole.

According to the invention, the drilling function and that of guiding have therefore been separated, which makes it possible to avoid, in the first hole, friction or blockages between the drill or its extension element which turn about themselves at high speed, and wear on parts that results from this friction.

According to an advantageous embodiment of the invention, said guiding of the drill is effected through cooperation of first guiding means, arranged on the surgical guide outside said at least one first hole, with second guiding means connected to the drill.

The surgical guide equipped with at least one artificial prosthesis and at least one first hole, each passing through an artificial prosthesis in a predetermined direction, may be produced according to various methods known per se. It is possible, for example, to cite the method of producing such a guide described in the patent application PCT/EP2006/050584, or again the techniques of stereolithography, digital milling and fast prototyping well known to the person skilled in the art. Advantageously, during production of the surgical guide, the method comprises placement therein of at least one hollow element, each hollow element being provided with an aforementioned first hole.

The present invention also relates to equipment intended for an implantation of a bone prosthesis in a bone of a patient, comprising:

at least one model produced from an impression of the skin or mucous membranes of the patient;
a surgical guide, produced from this impression and equipped with at least one artificial prosthesis and at least one first hole, each passing through an aforementioned artificial prosthesis in a predetermined direction and having an internal diameter;
at least one first drill that has an external diameter and which, when the surgical guide is in place on the model, is capable of drilling a second hole through the model in an identical direction to that of each aforementioned first hole, while passing through this;
an implant analog to be housed in each drilled second hole in the model;
an analog holder capable of holding, in a detachable manner, an aforementioned implant analog and of housing it in its second hole by sliding in the corresponding first hole, each analog holder being equipped with stop means capable of stopping it sliding when the implant analog in the second hole is in a position corresponding to a surgically appropriate position;
a bone prosthesis constructed on the model freed of the analog holder(s) and of the surgical guide;
at least one second drill which has an external diameter and which, when the surgical guide is in place on the patient's bone, is capable of passing through said first holes and of drilling third holes in the patient's bone in said predetermined direction, said at least one second drill comprising retaining means capable of stopping penetration of the second drill at a predetermined depth;
an implant to be housed in each third hole drilled in the bone; and
an implant holder capable of holding, in a detachable manner, an aforementioned implant and of housing it in its third hole, by axially sliding into the corresponding first hole, each implant holder being equipped with stopping means capable of stopping it sliding when the implant in the third hole is in a surgically appropriate position in which the implants are capable of receiving said bone prosthesis previously produced on the model.

This equipment is characterized in that:
the internal diameter of each aforementioned first hole is greater than the external diameter of said at least one first drill and said at least one second drill so that there is no contact between the drill and/or an extension element thereof and the first hole through which it is passed to carry out a drilling; and
the equipment furthermore comprises means for inserting the drill into each first hole that are external to each first hole and which guide the drill parallel to said first hole in the predetermined direction.

According to one embodiment of the equipment according to the invention, said means for inserting the drill comprise first guiding means arranged on the surgical guide outside said at least one first hole and second guiding means connected to each first or second drill and capable of cooperating with the first guiding means in order to guide the drill in said predetermined direction during the drilling. Advantageously, the first guiding means consist of at least one guiding hole which is provided in the surgical guide and which extends parallel to each first hole and the second guiding means consist of at least one guiding rod connected to the first or second drill, parallel to this and capable of penetrating into an aforementioned guiding hole in order to enable guiding of the first or second drill while drilling in the predetermined direction.

According to an improved embodiment, said first holes are formed from hollow elements placed in the surgical guide and each having an axial cavity that extends in said predetermined direction. The hollow elements are preferably provided with at least one guiding hole that extends parallel to said axial cavity.

Other particular features of the method and of the equipment according to the invention are indicated in the appended claims.

Further details of the invention will emerge from the description given below, without limitation and with reference to the appended drawings.

In the various figures, identical or like elements bear the same references.

FIG. 1 shows a surgical guide 1 in place on a model 2 produced from the impression of the patient's jaw.

In the example illustrated, the surgical guide 1 has been produced according to the technique explained in patent application PCT/EP2006/050584. As has already been mentioned, this guide might have been produced by other techniques. In order to produce the surgical guide illustrated, the procedure is implemented by shaping on the model of an arrangement equipped with false teeth adjustable in the mouth, by producing a key of the arrangement, by pouring a material visible by radiological imaging into the key mounted on the model after removal of the false teeth, by curing of this material in the form of an arc, by dividing the cured arc of individual radiological artificial teeth which, when replaced in the key, are fixed on the model and, after removing the key, by producing a radiological guide by depositing a self-curing resin on the radiological artificial teeth fixed to the model, this radiological guide being provided with radiological markers. Next, by computer processing a two-dimensional radiological image representing the radiological guide in position on the jaw, a three-dimensional image is constituted. In these two- and three-dimensional images a virtual implant is then inserted, per tooth, in a surgically appropriate position in the image of the jaw and a virtual hollow element having a cavity coaxial with the virtual implant is placed in the image of the radiological guide. From the data collected and calculated by the computer during these image processing steps, a surgical guide is produced by drilling, in the aforementioned radiological guide and through each artificial tooth 15, a bore suitable for receiving a real hollow element 3 provided with an axial cavity 4 forming a first hole and directed in a predetermined direction, that of the virtual implant in the image of the radiological guide.

Figure 1:
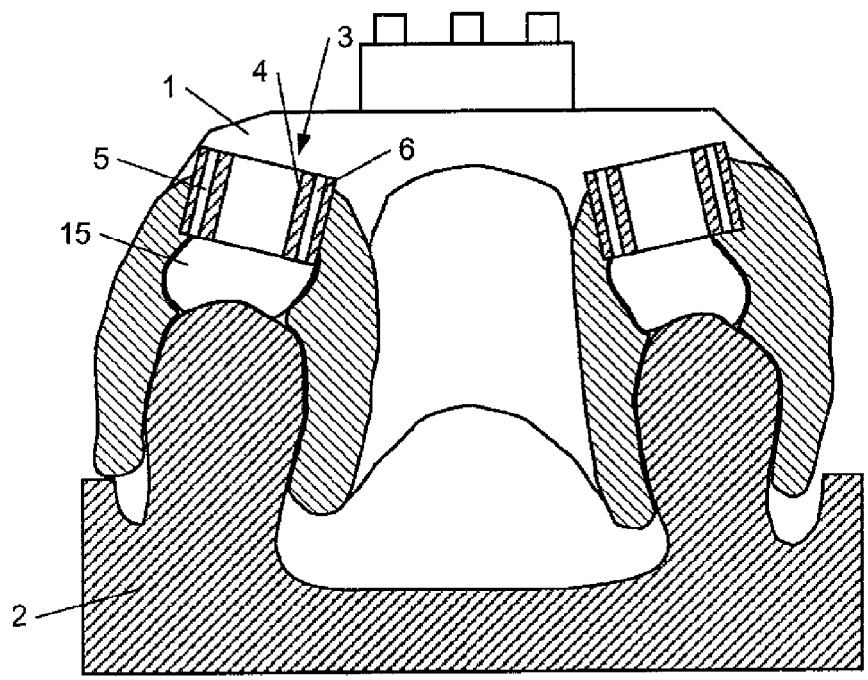
FIGS. 1 to 5 show a sectional view of a model during the steps of implantation of implant analogs therein and of producing the final prosthesis on the implant analogs.
Figure 6:
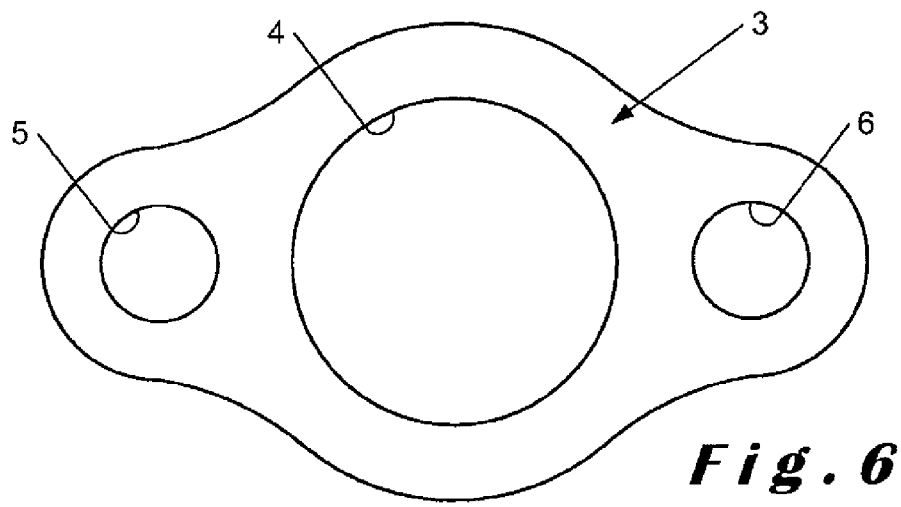
FIG. 6 shows a plan view from above of a hollow element to be placed in a surgical guide of the equipment according to the invention.
Figure 7:
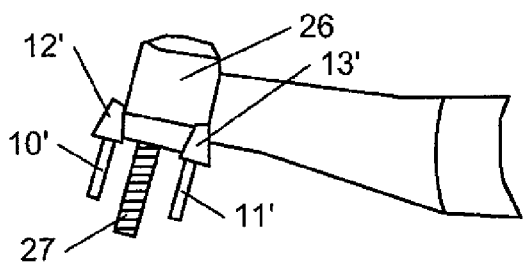
FIG. 7 shows a contra angle equipped with a drill and with guiding means according to the invention.

In the example illustrated in particular in FIGS. 1 and 6, the hollow element 3 has, on both sides of the axial cavity 4, guiding holes 5 and 6 which are situated outside the axial cavity 4 and extend parallel to this cavity.

Figure 2:
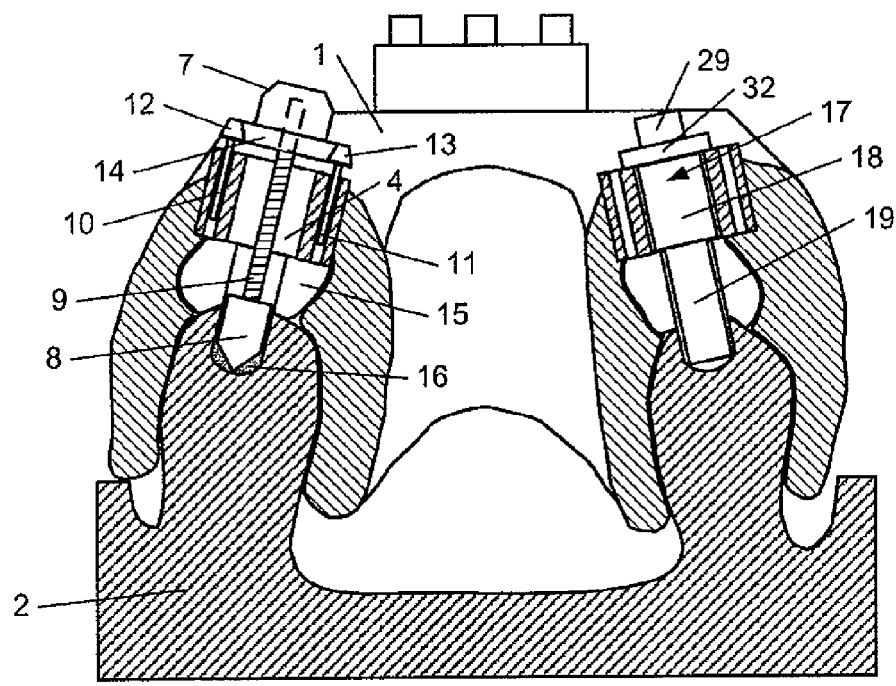

On the other hand, as FIG. 2 shows, drilling apparatus 7 represented only in a schematic manner is provided with a drill 8 that is passed through the axial cavity 4 and which may be driven rotationally by a motor (not shown) of the drilling apparatus by means of a support rod 9 that is used as an extension element of the drill 8.

The drilling apparatus 7, and hence the drill 8, are also equipped, in the example illustrated, with two guiding rods 10 and 11 which extend parallel to the drill and are capable of penetrating into the guiding holes 5 and 6. These rods are topped by stops 12 and 13 having a diameter greater than the internal diameter of the holes 10 and 11. They are advantageously connected to the drilling apparatus 7 and to the support rod 9 by a collar 14 such that the support rod 9 is able to turn about its axis and the drilling apparatus 7 is able to carry out a rotation, preferably of 360°, about the support rod when the guiding rods 10 and 11 have already been at least partly inserted into the guiding holes 5 and 6.

It must be understood that, if techniques different from that used for the example illustrated are applied for producing the surgical guide, it is possible to shape the first hole corresponding to the axial cavity 4 and the guiding holes 5 and 6 directly in the mass of the surgical guide 1 without having to place a hollow element 3 therein.

Depending on the depth of drilling desired, the length of the drill will be chosen by taking account both of the guiding length of the rods 10 and 11, until the stops 12 and 13 stop the travel of the drill 8, and of the depth to which the drill extension element is inserted into the drilling apparatus 7.

Figure 3:
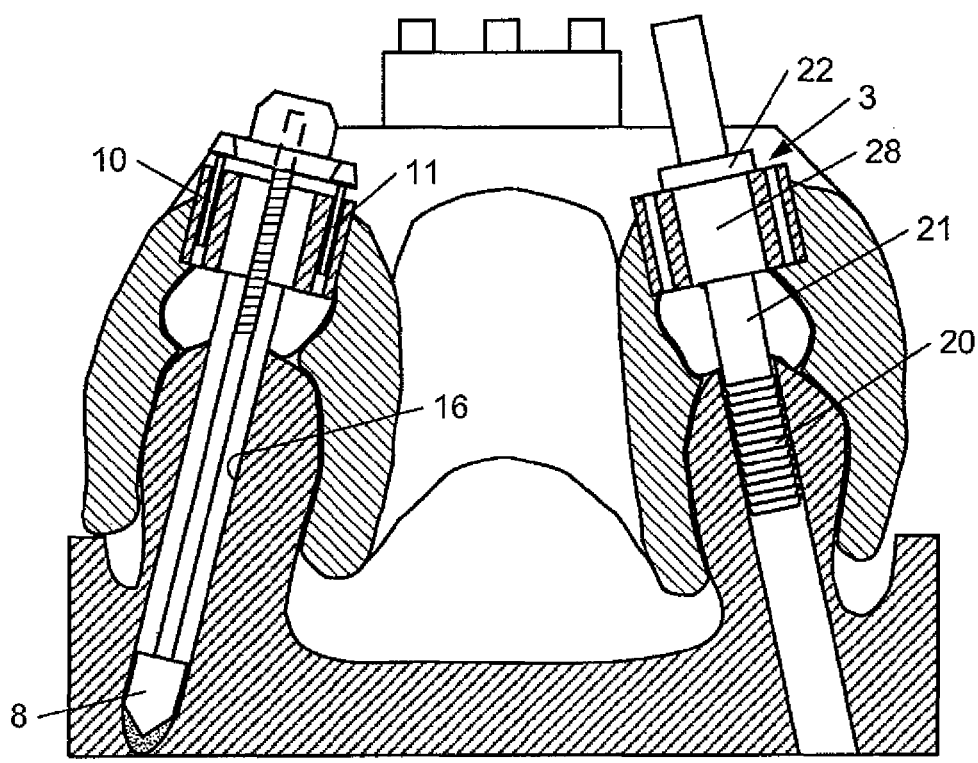

In the example illustrated in FIGS. 2 and 3, the drilling is carried out in several steps. In the left part of FIG. 2, a drill 8 is passed through the axial cavity 4 or the first hole of the surgical guide without coming into contact with the walls of this cavity. The drill 8 and the extension rod 9 in fact have an external diameter less than the internal diameter of the axial cavity 4. In addition, the guiding rods 10 and 11 that penetrate into the guiding holes 5 and 6 guide the drill in the predetermined direction of the cavity, i.e. axially. All contact between the drill 8 and the hollow element 3 is thus avoided during drilling, which enables the drawbacks of the prior art to be overcome. It should be noted that a single guiding hole and a corresponding single guiding rod would already suffice. In the course of drilling, the drill 8 drills a second hole 16 in the model 2, until the stops 12 and 13 stop any additional penetration.

It is then possible to remove the drilling apparatus 7 and extract the drill 8 outside the hollow element 3. Before starting to drill a new second hole in the model, a placeholding element 17 is inserted into the second hole 16 drilled in the initial drilling step, which placeholding element ensures the position of the surgical guide 1 on the model 3 while another second hole is drilled. This placeholding element 17 is illustrated, in use, on the right part of FIG. 2.

This placeholding element 17 comprises, at the center, a smooth cylindrical body 18 which is adapted to the dimensions of the axial cavity 4 of the hollow element. At one end, this cylindrical body is extended by a rod 19 adapted to the dimensions of the second hole 16, and at the opposite end it is provided with a collar 32 of larger diameter than the first hole formed by the axial cavity 4 and with a handle 29. This element is thus capable of locking the surgical guide into place on the model while a neighboring second hole 16 is drilled.

When all the second holes have been drilled to a first depth, it is possible to continue the drilling to a second depth. In this case, the placeholding element 17 of one hollow element 3 is removed, while the others are left in place. A second drill with a longer extension rod 9 is then inserted and drilling takes place in the same manner as previously described, i.e. in a manner guided by the guiding rods 10 and 11 and the guiding holes 5 and 6. It is thus possible to arrive at the depth attained on the left part of FIG. 3 and to pass completely through the model.

Figure 4:
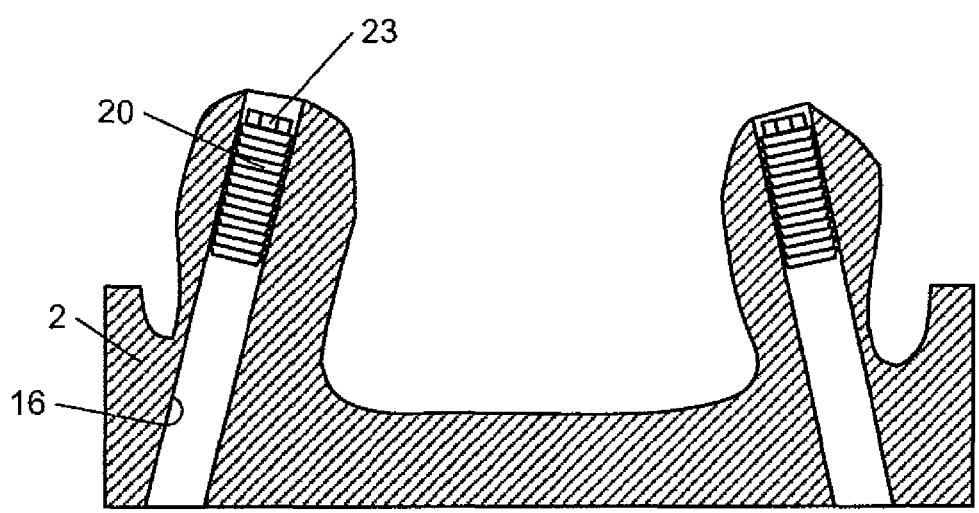

As illustrated on the right part of FIG. 3, it is then possible to insert into the second hole 16 an implant analog 20 having dimensions corresponding to those of a real implant to be placed in the patient's jaw. This placement is carried out by means of an analog holder 21 which comprises a cylindrical part 28 capable of sliding in a guided manner into the axial cavity 4 of the hollow element 3 and which is capable of bringing the implant analog 20 to the required depth in the second hole 16. To this end, the analog holder 21 has a collar 22 which stops the sliding of the implant analog 20 in the corresponding second hole 16. The analog holder may optionally also cause the implant analog 20 to turn into an appropriate angular position, which might be necessary when this holds, as illustrated in FIG. 4, a head 23 of polygonal cross section.

Figure 5:
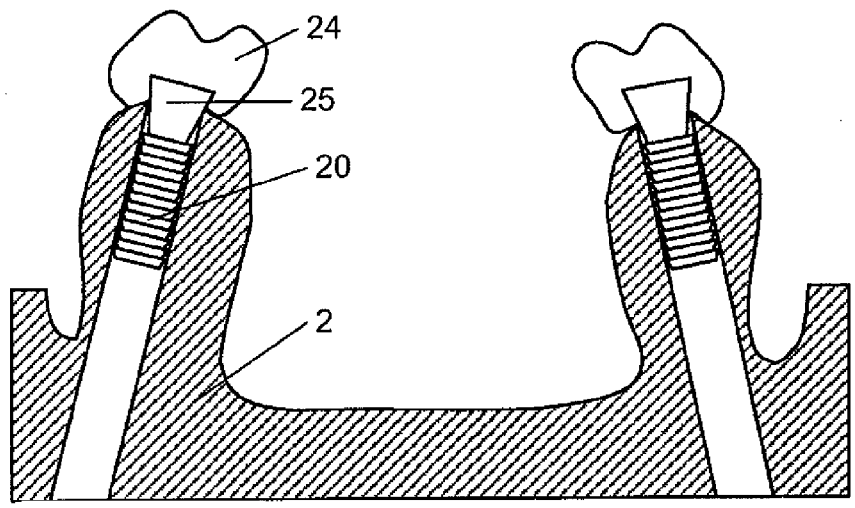

The implant analog can then be fixed in position in the hole 16, for example by a suitable adhesive that is introduced into the hole 16 through the model 2. The analog holder can then be removed (see FIG. 4). The model is ready for producing a preimplant simulation in the form of a final prosthesis, for example bars, crowns or bridges. A prosthesis in position on the model is illustrated in FIG. 5, where a joining element 25 has been fixed to each implant analog with the final corresponding artificial tooth 24 above.

Next, the surgical guide 1, equipped with its first holes and corresponding guiding holes, i.e. in the example illustrated the hollow elements 3, is placed in the patient's mouth.

Use is then made of suitable drilling apparatus, known per se, for example a contra angle 26. This has a drill 27 having a diameter less than the internal diameter of the axial cavity 4. Like the drilling apparatus 7, the contra angle 26 is equipped with guiding rods 10' and 11' that are able to slide into the guiding holes 5 and 6 of the hollow elements. The stops 12' and 13' stop the drilling at a predetermined depth, which here too can be carried out in several steps. Here too it is preferable to drill each third hole in the jaw to a first depth before drilling one to a greater depth. While one third hole is being drilled, the others receive a placeholding element 17 that ensures the position of the surgical guide on the jaw. During the last drilling, the drills, in addition to being guided in a correct direction by the guiding holes and rods, are stopped in their sliding by the stops 12', 13' that the guiding rods hold at an appropriate height corresponding to the depth of the implant on the two- and three-dimensional images.

An implant similar to the implant analog is then inserted into each of these holes using an implant holder similar to the analog holder, i.e. provided with a means of stopping the sliding, in the form of a collar for example. The implant is thus set in at the required depth in the appropriate direction. Using a marker, the implant holder may optionally rotate the head of the implant with a cross section identical to that of the implant analog to the same angular position as the head of the implant analog on which the prosthesis has been shaped.

The position of the implants in the mouth is unique and it corresponds perfectly to that of the implant analogs in the model, as well as to that appearing in the two- and three-dimensional radiological images. It is therefore possible to place there directly the prosthesis that has been produced before the application of the implants.

An advantage of this technique is also that thanks to the prosthetic anticipation the exact relative positions of the implants/prosthesis/bone are known and that all the tolerances of depth, rotation and lateral positions are determined and fixed. In this way all human errors by drilling are excluded.

The apparatus according to the invention furthermore enables perfect guiding of the contra angle without the drill risking blockage or friction with the walls of the axial cavity of the hollow elements. In this way any risk of fracturing the internal part of the contra angle and of metal particles penetrating into the implantation site is eliminated. Finally, heating of the drill is no longer produced by friction between the guiding part of the drill and the axial cavity of the hollow element. A burn at the bone level is thus avoided.

In addition the irrigation and cooling fluids of the drill are no longer blocked by the guiding part of the drill.

It should be understood that the present invention is in no way limited to the embodiments described above and that modifications may be made to it without departing from the scope of the appended claims.

It is possible, for example, to provide guiding rods 10 and 11 that are longer than those provided in the example illustrated, in particular in order to be able to produce drilling in fewer steps, or even in a single step. In this case, during the development of the surgical guide 1, the boring of the artificial teeth 15 is carried out in a manner appropriate not only for receiving the hollow element 3, but also for being able to insert the guiding rods 10 and 11 when they pass beyond the hollow element 3 after having passed through the guiding holes 5, 6 thereof.

It is also even possible, during the computer processing of the radiological image of the radiological guide in position on the jaw, to insert into the 2D or 3D image virtual guiding rods enabling the previously described boring of the radiological guide to be correspondingly controlled as a surgical guide capable of receiving real guiding rods.

Figure 8:
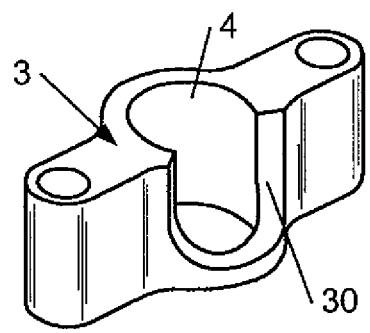
FIGS. 8 and 9 show, in a perspective view, a variant of the hollow element according to the invention and its holder element.

FIG. 8 furthermore shows a hollow element designed to be placed on the surgical guide at locations that are difficult to access, for example the parts behind the jaws. In relation to the hollow element shown in FIG. 6, this has a lateral recess 30 which enables radial access to the axial cavity 4. This arrangement facilitates the penetration of the contra angle and of its drill into the hollow element by radial insertion then rotation by 90°.

Figure 9:
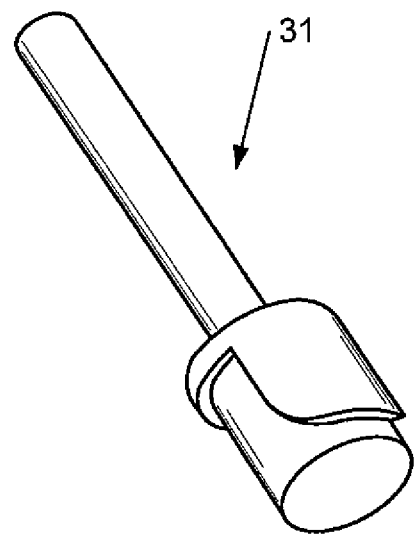

FIG. 9 shows the corresponding hollow element holder 31, which enables the hollow element to be placed in the surgical guide.

The invention claimed is:

1. Equipment intended for an implantation of a bone prosthesis in a bone of a patient, comprising:
   a surgical guide (1) having at least one first hole (4), said first hole having an internal diameter;
   a drill (8) having an external diameter, said drill being capable of passing through each first hole (4) in order to carry out drilling by means of a drilling apparatus (7), wherein:
   the internal diameter of each first hole (4) is greater than the external diameter of the drill (8) so that there is no contact between the drill and the first hole (4) through which it is passed to carry out the drilling; and wherein the surgical guide (1) furthermore comprises:
   1. at least one guiding hole (5, 6) situated outside said at least one first hole (4), and
   2. a second guiding means:
      a. capable of being connected to the drilling apparatus (7); and
      b. comprising at least one guiding rod (10, 11) extending parallel to the drill (8) while the second guiding means are connected to the drilling apparatus, the at least one guiding rod (10, 11) being capable of penetrating into the at least one guiding hole (5, 6) in order to allow guiding of the drill (8) during drilling through the first hole (4).

2. The equipment as claimed in claim 1, wherein it comprises at least one hollow element (3) capable of being placed in the surgical guide (1), each hollow element (3) having an axial cavity (4) forming an aforementioned first hole (4) and at least one hole (5, 6) forming an aforementioned guiding hole.

3. The equipment as claimed in claim 2, wherein at least one hollow element (3) has a lateral recess (30) enabling radial access into the axial cavity (4).

4. The equipment as claimed in claim 1, wherein the second guiding means comprise at least one stop (12, 13, 12', 13') capable of stopping the travel of the drill (8).

5. The equipment as claimed in claim 1 or in claim 4, wherein the second guiding means are capable of being connected to the drilling apparatus (7) in a rotational manner about an axis of the drill (8).

6. The equipment as claimed in claim 5, wherein the second guiding means are capable of being connected to the drilling apparatus (7) so as to rotate 360° about an axis of the drill.

* * * * *